(12) United States Patent
Inoue et al.

(10) Patent No.: US 8,535,498 B2
(45) Date of Patent: Sep. 17, 2013

(54) ELECTROCHEMICAL GAS SENSOR AND METHOD FOR CLAMPING THE SAME

(75) Inventors: Tomohiro Inoue, Tokyo (JP); Yuki Kato, Osaka (JP); Keiko Shibata, Osaka (JP)

(73) Assignee: Figaro Engineering Inc., Osaka (JP)

( * ) Notice: Subject to any disclaimer, the term of this patent is extended or adjusted under 35 U.S.C. 154(b) by 37 days.

(21) Appl. No.: 13/429,756

(22) Filed: Mar. 26, 2012

(65) Prior Publication Data
US 2013/0068616 A1   Mar. 21, 2013

(30) Foreign Application Priority Data

Apr. 5, 2011 (JP) ................................. 2011-083487
Mar. 1, 2012 (JP) ................................. 2012-045040

(51) Int. Cl.
*G01N 27/403* (2006.01)

(52) U.S. Cl.
USPC ............. 204/424; 204/431; 422/88; 205/781; 205/782; 73/23.31; 73/23.32; 73/31.01

(58) Field of Classification Search
USPC ................... 422/88; 204/421–431; 205/781, 205/782; 73/23.31, 23.32, 31.01
See application file for complete search history.

(56) References Cited

U.S. PATENT DOCUMENTS

| | | | |
|---|---|---|---|
| 5,573,648 A * | 11/1996 | Shen et al. ..................... 204/412 |
| 5,650,054 A | 7/1997 | Shen et al. |
| 2005/0121338 A1* | 6/2005 | Inoue ........................... 205/775 |
| 2006/0120924 A1* | 6/2006 | Inoue et al. ..................... 422/88 |

FOREIGN PATENT DOCUMENTS

| JP | 2004-226346 A | 8/2004 |
|---|---|---|
| JP | 2006-84319 A | 3/2006 |

\* cited by examiner

*Primary Examiner* — J. Christopher Ball
*Assistant Examiner* — Jennifer Dieterle
(74) *Attorney, Agent, or Firm* — Keating & Bennett, LLP

(57) ABSTRACT

An electrochemical gas sensor includes: a disc-shaped metal bottom member; a cylindrical metal side member that extends along the axial direction of the bottom member to surround the bottom member; a ring-shaped polymer gasket that includes an opening in the center and in which both sides of the opening each have an L-shaped member in cross section, with one section of the L-shaped member being in contact with the inner side of the side member and the other section of the L-shaped member being in contact with the bottom member; a gas sensor body that is located in the opening of the gasket and whose bottom surface is in contact with the bottom member and that includes a pair of electrodes and a solid electrolyte membrane or a separator retaining a liquid electrolyte; and a metal cover that is in contact with the top surface of the gas sensor body.

4 Claims, 7 Drawing Sheets

3

12

Embodiment

Prior Art

ELECTROCHEMICAL GAS SENSOR AND METHOD FOR CLAMPING THE SAME

BACKGROUND OF THE INVENTION

1. Field of the Invention

The present invention relates to an electrochemical gas sensor, and more particularly to a method for clamping the same.

2. Description of Related Art

The present inventors have developed electrochemical gas sensors in which the bottom of a gas sensor body is disposed in a metal container, a cover is disposed on the top surface of the gas sensor body, and the cover and the container are clamped via a gasket (Patent Document 1: JP 2004-226346A and Patent Document 2: JP 2006-84319A). Patent Document 1 discloses a configuration in which the tip end of the container is bent at a right angle from the axial direction of the container so as to press the gasket downward. Patent Document 2 discloses a configuration in which the gasket is in contact with the tip end of the container but is not provided near the gas sensor body. Patent Document 3 (U.S. Pat. No. 5,650,054) discloses a configuration in which a cover is received in the recess of a gasket.

Electrochemical gas sensors exhibit variation in their gas sensitivity, and those equipped with a water reservoir exhibit variation in the water evaporation amount as well. The variation in the gas sensitivity requires accurate adjustment of attached circuitry or reduces the yield of the gas sensor. Also, the variation in the water evaporation amount brings about variation in the service life of the gas sensor.

Patent Document 1: JP 2004-226346A
Patent Document 2: JP 2006-84319A
Patent Document 3: U.S. Pat. No. 5,650,054

SUMMARY OF THE INVENTION

It is an object of the present invention to reduce the variation in the gas sensitivity of electrochemical gas sensors.

The present invention provides an electrochemical gas sensor including: a disc-shaped metal bottom member; a cylindrical metal side member that extends in at least a first direction along an axial direction of the bottom member so as to surround the bottom member; a ring-shaped polymer gasket that includes an opening in the center and in which both sides of the opening each have an L-shaped member in cross section, with one section of the L-shaped member being in contact with an inner side of the side member and the other section of the L-shaped member being in contact with the bottom member; a gas sensor body that is located in the opening of the gasket and whose bottom surface is in contact with the bottom member, the gas sensor body including at least a pair of electrodes and a solid electrolyte membrane or a separator retaining a liquid electrolyte; and a metal cover whose bottom surface is circular and is in contact with a top surface of the gas sensor body, wherein the cover includes a ring-shaped protrusion provided around periphery of the cover and extending to a side opposite the bottom surface along the axial direction of the cover, and a tip end of the side member and a tip end of the one section of the L-shaped member of the gasket are bent at an acute angle toward the bottom member from the first direction, the tip end of the side member, the tip end of the one section of the L-shaped member of the gasket and a tip end of the protrusion of the cover are in hermetic contact with each other, and none of the three tip ends is parallel to a surface of the bottom member.

A method for clamping an electrochemical gas sensor according to the present invention is a method for clamping an electrochemical gas sensor including: a disc-shaped metal bottom member; a cylindrical metal side member that extends in at least a first direction along an axial direction of the bottom member so as to surround the bottom member; a ring-shaped polymer gasket that includes an opening in the center and in which both sides of the opening each have an L-shaped member in cross section; a gas sensor body including at least a pair of electrodes and a solid electrolyte membrane or a separator retaining a liquid electrolyte; and a metal cover having a circular bottom surface, the cover including a ring-shaped protrusion provided around periphery of the cover and extending to a side opposite the bottom surface along the axial direction of the cover, the method including the steps of: disposing the gasket, the gas sensor body and the cover on the bottom member such that the one section of the L-shaped member of the gasket is surrounded by the side member and the other section is in contact with the bottom member, that the gas sensor body is located in the opening of the gasket and a bottom surface of the gas sensor body is in contact with the bottom member, and that the bottom surface of the cover covers a top surface of the gas sensor body and the ring-shaped protrusion of the cover extends to a side opposite the bottom member; and bringing a surface of a hole of a mold tapered to have a larger diameter at front and a smaller diameter at rear into contact with a tip end of the side member, whereby the tip end of the side member and a tip end of the one section of the L-shaped member of the gasket are bent at an acute angle toward the bottom member from the first direction, the tip end of the side member, the tip end of the one section of the L-shaped member of the gasket and a tip end of the protrusion of the cover are in hermetic contact with each other, and the three tip ends are clamped such that none of them is parallel to a surface of the bottom member.

According to the present invention, the three tip ends can be hermetically clamped to each other. Also, the gap between the other section of the L-shaped member of the gasket and the bottom member and the gap between the other section of the L-shaped member of the gasket and the cover is eliminated. As a result, the constituent members of the electrochemical gas sensor are accurately positioned, and the variation in gas sensitivity is reduced. When the present embodiment is compared to a comparative example in which, for example, the angle of the tip end of the side member from the first direction is set to 90°, in the present embodiment, the distribution of gas sensitivity can be narrowed as compared to that of the comparative example (FIGS. 13 and 14). The angle of the tip end of the side member is preferably 10° to 60° from the first direction, and particularly preferably 20° to 50°.

Preferably, the side member extends in a direction opposite to the first direction from a position of the bottom member and constitutes a bottomed cylindrical container, the bottom member is held by a waist portion of the cylindrical container, water is stored in a bottom space of the cylindrical container that is below the bottom member, and the bottom member is provided with a hole. The water may be liquid water or water gelled with silica or the like. Besides plain water, water containing an electrolyte such as a sulfonic acid compound may be used. According to the present invention, as shown in FIG. 12, the variation in the amount of water evaporated from the water reservoir can be reduced, and thus the variation in the service life of the gas sensor can be reduced.

DETAILED DESCRIPTION OF THE PREFERRED EMBODIMENT

Figure 1:
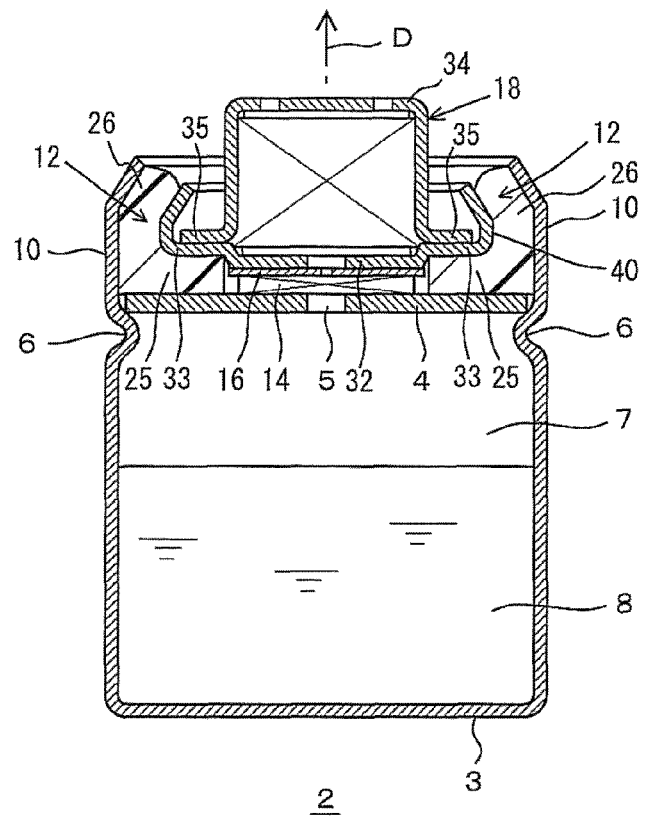
FIG. 1 is a vertical cross-sectional view of an electrochemical gas sensor according to an embodiment of the present invention.

Hereinafter, best modes for carrying out the present invention will be described.

Embodiment

FIGS. 1 to 14 show an embodiment of the present invention and characteristics thereof. FIGS. 1 to 6 show a structure of an electrochemical gas sensor 2 of the present embodiment. Reference numeral 3 indicates a bottomed cylindrical container made of metal, and reference numeral 4 indicates a bottom plate that is made of a metal disc and provided with a hole 5. The bottom plate 4 is supported by a waist 6 formed in the container 3. A lower part of the container 3 that is below the waist 6 constitutes a water reservoir 7 in which water 8 is stored. The water may be plain water, or may be water containing an electrolyte, water gelled with silica or the like, water containing deliquescent salt, or water held by water absorbent polymer or the like.

An upper part of the container 3 that is above the bottom plate 4 is referred to as a side portion 10, and the side portion 10 has a cylindrical shape. A gasket 12 is disposed on the bottom plate 4, and a gas sensor body 14 is placed in a center opening of the gasket 12. An atmosphere to be detected is supplied via a circular diffusion control plate 16 as viewed from above. A metal cover 18 is disposed so as to cover the diffusion control plate 16. The cover 18 is rotationally symmetric about an axial direction D. Clamping the tip end (upper part in the diagrams) of the side portion 10 provides a hermetic seal between the side portion 10 and the gasket 12 and between the gasket 12 and the cover 18 and causes the cover 18 to be attached to the container 3.

Figure 2:
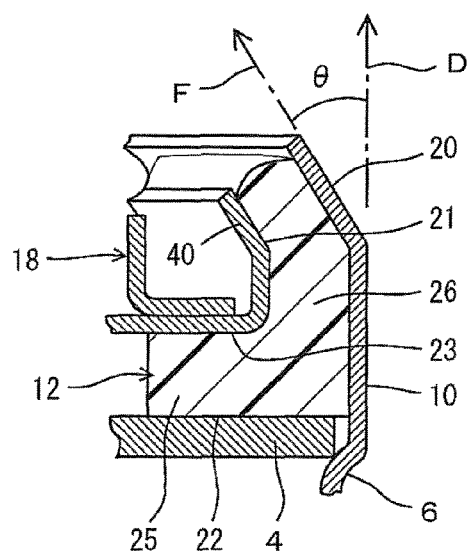
FIG. 2 is an enlarged cross-sectional view of a relevant part of the electrochemical gas sensor shown in FIG. 1.

FIG. 2 shows a major part of the present embodiment. Reference letter D indicates the axial direction of the gas sensor 2. The axial direction D is the axial direction of the bottom plate 4, the cover 18 and the container 3, and corresponds to the first direction recited in the claims. Reference letter F indicates the direction of the tip end of the side portion 10, and the tip end direction F is angled obliquely with respect to the axial direction D and points toward the center of the bottom plate 4. The angle between the directions D and F is defined as an angle of inclination θ. The angle of inclination θ can range from 0° to 90°, and is preferably 10° to 60° and more preferably 20° to 50°. As used herein, the terms "above" and "up" refer to the direction in which the axial direction D points, and the terms "below" and "down" refer to the opposite direction to the axial direction D. The term "right and left" refers to the direction that is parallel to the surface of the bottom plate 4 and perpendicular to the axial direction D. The shape of the respective members of the present embodiment does not change even when they are rotated about the axial direction as the axis of rotation, and is circular as viewed from above.

By the tip end of the side portion 10 being clamped, the tip end is bent obliquely inwardly with respect to the axial direction D, as a result of which the tip end of the gasket 12 is also bent obliquely inwardly and the tip end of the cover 18 is also bent obliquely inwardly. Reference numeral 20 indicates a contact portion between the side portion 10 and the gasket 12, and reference numeral 21 indicates a contact portion between the gasket 12 and the cover 18. The contact portions 20 and 21 need to be hermetically sealed, and they are preferably parallel to each other. Reference numeral 22 indicates a contact portion between the bottom surface of the gasket 12 and the bottom plate 4, and it is preferable that there is no gap in the contact portion. Reference numeral 23 indicates a contact portion between the top surface of the gasket 12 and the bottom surface of the cover 18, and it is preferable that they are in contact without a gap therebetween.

Figure 3:
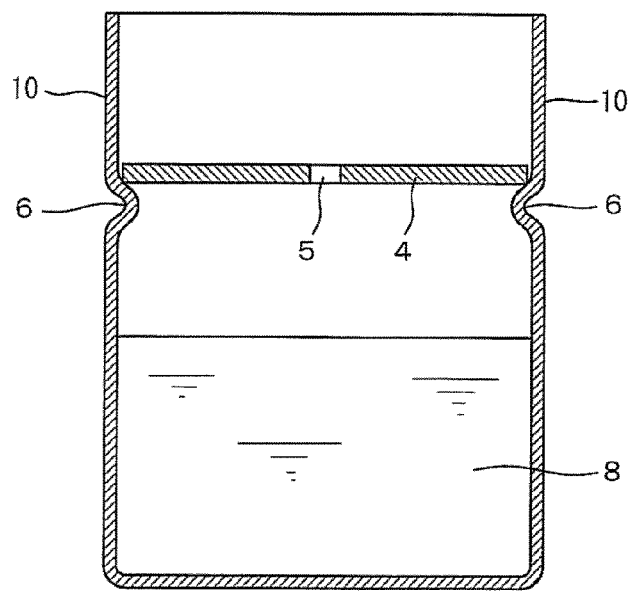
FIG. 3 is a vertical cross-sectional view of a container and a bottom plate of the electrochemical gas sensor shown in FIG. 1.
Figure 4:
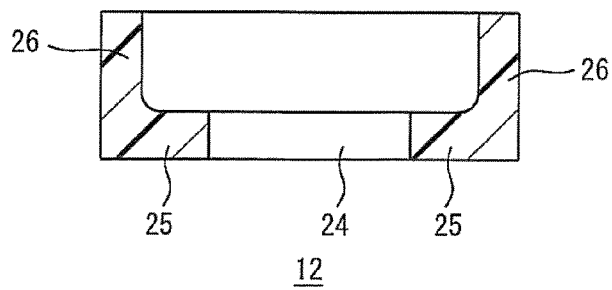
FIG. 4 is a vertical cross-sectional view of a gasket of the electrochemical gas sensor shown in FIG. 1.

FIG. 3 shows the shape of the container 3 before the gasket 12 and the like are attached. The side portion 10 extends in a ring upward from the bottom plate 4. FIG. 4 shows a structure of the gasket 12. The gasket 12 is circular as viewed from above and has a circular opening 24 in the center. The right and left sides of the gasket 12 are L-shaped membered in vertical cross section and are composed of a ring-shaped bottom portion 25 and a protrusion 26 protruding in a ring upward from the periphery of the bottom portion 25. The gasket 12 is preferably made of plastic having plasticity and elasticity such as polyethylene, polypropylene, nylon or tetrafluoroethylene, or may be natural rubber, synthetic rubber or the like.

Figure 5:
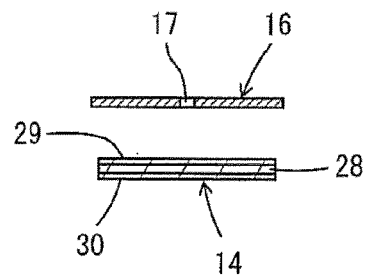
FIG. 5 is a cross-sectional view of a gas sensor body and a diffusion control plate of the electrochemical gas sensor shown in FIG. 1.

FIG. 5 shows the gas sensor body 14 and the diffusion control plate 16, which are circular in shape. Reference numeral 28 indicates a separator in the form of a film made of porous paper or plastic and retaining a liquid electrolyte. A sensing electrode 29 and a counter electrode 30 are provided, for example, on the top and bottom surfaces of the separator 28. The sensing electrode 29 and the counter electrode 30 are each made of a porous carbon sheet or the like carrying electrode materials such as platinum and carbon. It is also possible to use a solid electrolyte membrane or the like, instead of the separator 28. It is also possible to dispose a porous carbon fiber sheet or the like between the sensing electrode 29 and the diffusion control plate 16 and between the counter electrode 30 and the bottom plate 4. The diffusion control plate 16 is a thin plate made of titanium or the like and includes a diffusion control hole 17. The diffusion control plate 16 controls supply of the atmosphere to the sensing electrode 29 and electrically connects the sensing electrode 29 and the cover 18. The counter electrode 30 is electrically connected to the container 3 via the bottom plate 4.

Figure 6:
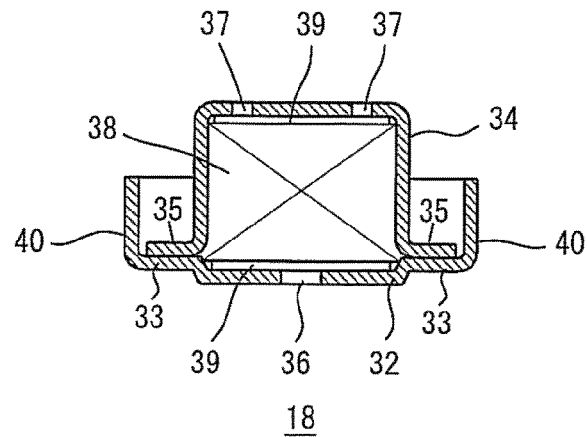
FIG. 6 is a vertical cross-sectional view of a cover of the electrochemical gas sensor shown in FIG. 1.

FIG. 6 shows a structure of the cover 18. Reference numeral 32 indicates a lower metal member, and reference numeral 34 indicates an upper metal member. These metal members are welded to each other. The space between the metal members 32 and 34 is filled with a filter member 38 such as activated carbon, and retaining sheets 39 are provided to prevent the filter member from spilling. The atmosphere is supplied toward the diffusion control plate 16 via holes 36 and 37. The metal member 32 provided on the diffusion control plate 16 side (lower side) includes a ring-shaped flange portion 33 on its outer periphery, and a ring-shaped protrusion 40 is formed by bending the outer periphery of the flange portion 33 upward. The lower metal member 32 is disc-shaped, the flange portion 33 is in contact with the top surface of the bottom portion 25 of the L-shaped member of the gasket 12, and the protrusion 40 is brought into hermetic contact with the inner surface of the protrusion 26 of the L-shaped member of the gasket 12 by clamping. The outer periphery of the upper metal plate 34 serves as a flange portion 35 by being bent so as to be parallel to the bottom plate 4, and the flange portions 33 and 35 are welded to each other.

Figure 7:
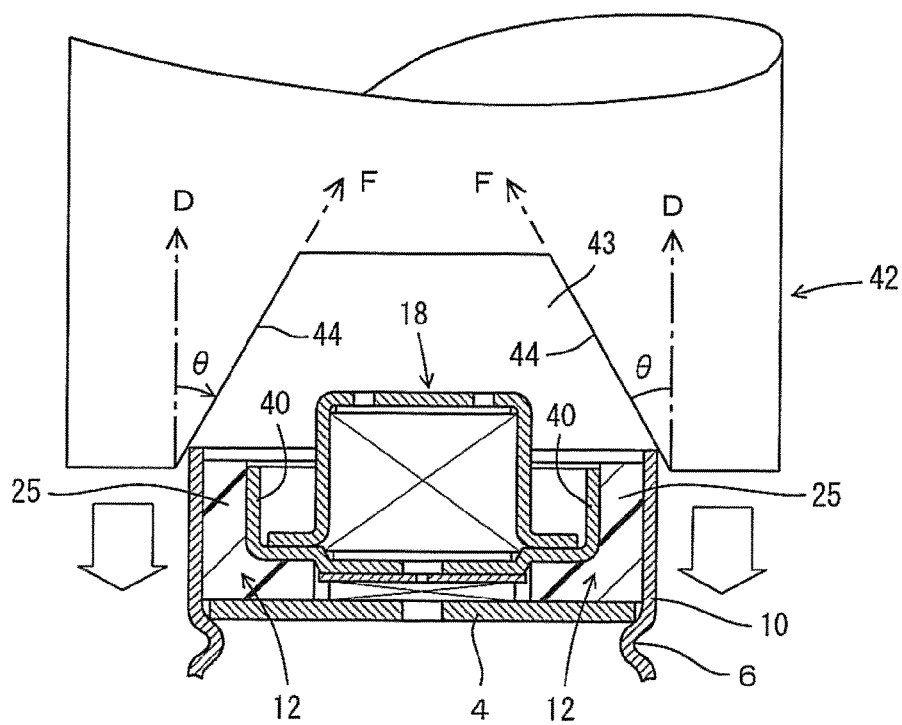
FIG. 7 is a diagram illustrating a method for clamping an electrochemical gas sensor according to an embodiment of the present invention.

FIG. 7 illustrates a method for clamping the electrochemical gas sensor 2. In the state shown in FIG. 3, the gasket 12 is placed on the bottom plate 4, the gas sensor body 14 and the diffusion control plate 16 are placed in the opening of the gasket 12, and the cover 18 is placed so as to cover the diffusion control plate. It should be noted that the order of placing these constituent elements can be set as appropriate. Reference numeral 42 indicates a press mold having a conical hole 43 in a center portion thereof, and clamping is performed by pressing and deforming the side portion 10 with a conical surface 44. In FIG. 7, the angle between the surface 44 and the axial direction D is substantially equal to the angle $\theta$ between the tip end of the side portion 10 and the axial direction D.

In the present embodiment, the diffusion control plate 16 is provided in order to make the amount of atmosphere supplied to the gas sensor body 14 constant, but it may be omitted. Also, the gas sensor body 14 may be disc-shaped as viewed from above, and the structure and material thereof can be selected as appropriate. A reference electrode may be provided in addition to the sensing electrode and the counter electrode. The present invention is provided to clamp the cover 18, the gasket 12 and the container 3, and therefore parts other than the parts described above can be modified according to known techniques.

Figure 8:
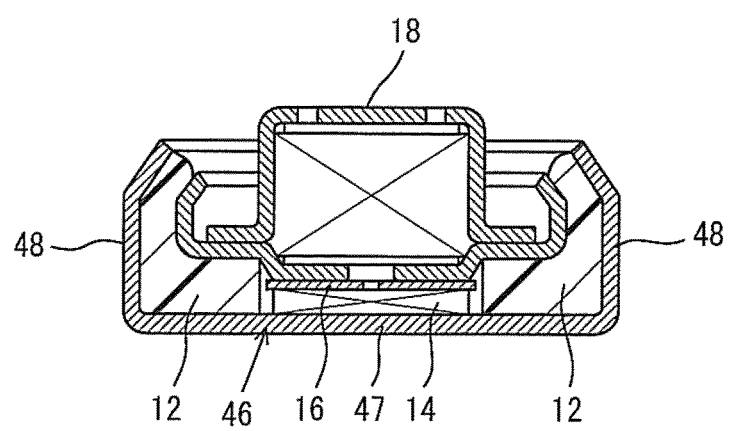
FIG. 8 is a vertical cross-sectional view of an electrochemical gas sensor according to a first variation of the embodiment.

FIG. 8 shows a gas sensor according to a variation, in which a container 46 without a water reservoir is used instead of the container 3 with a water reservoir. Accordingly, the gasket 12 and the gas sensor body 14 are disposed on a bottom portion 47 of the container 46, and the side portion 10 is replaced by a ring-shaped protrusion 48 provided on the outer periphery of the container 46. Other than those changes, the gas sensor according to this variation is the same as that of the present embodiment.

Figure 9:
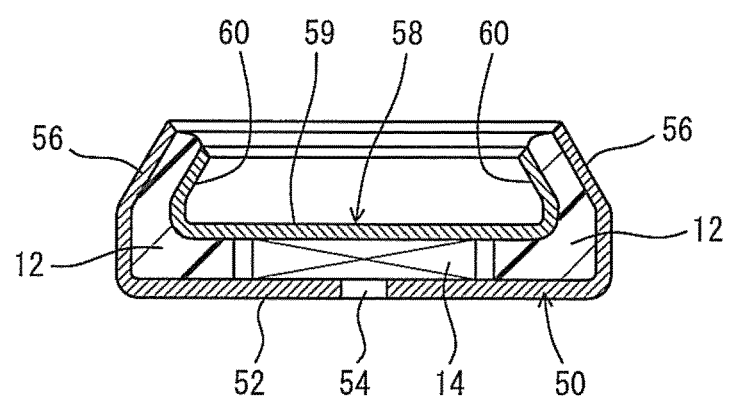
FIG. 9 is a vertical cross-sectional view of an electrochemical gas sensor according to a second variation of the embodiment.

FIG. 9 shows a second variation in which the filter member 38 is not used. Accordingly, a container 50 having a hole 54 is used, and the gasket 12 and the gas sensor body 14 are disposed on a bottom portion 52 of the container 50. In this example, the diffusion control plate 16 is not provided because the thickness of the gas sensor body 14 is increased. Also, a metal cover 58 is used, and the bottom surface of the cover 58, serving as a cover 59, is brought into contact with the gasket 12 and the gas sensor body 14. A ring-shaped upward protrusion 60 is provided around periphery of the cover 59, and the protrusions 56 and 60 are clamped via the gasket 12. Other than those changes, the gas sensor according to this variation is the same as that of the present embodiment.

Figure 10:
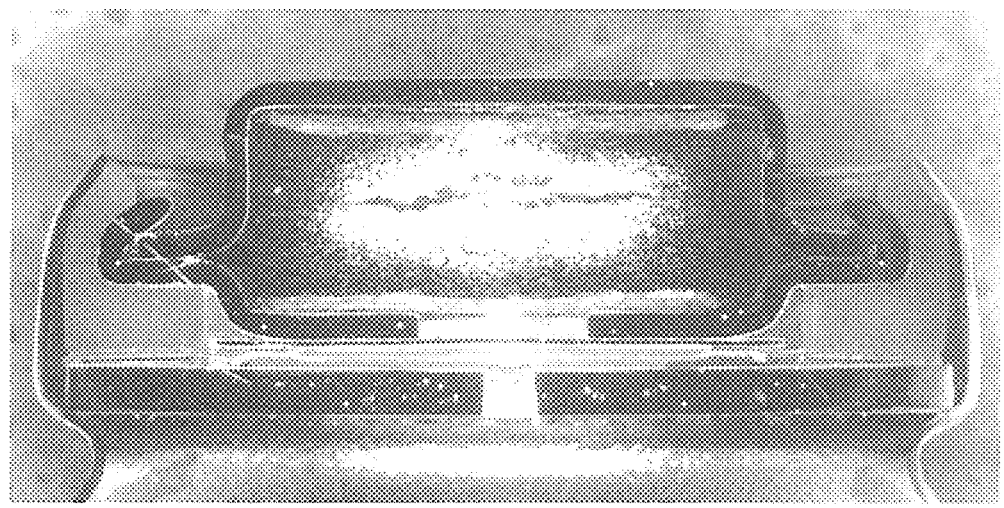
FIG. 10 is a photograph showing a vertical cross section of a relevant part of the electrochemical gas sensor according to the embodiment.
Figure 11:
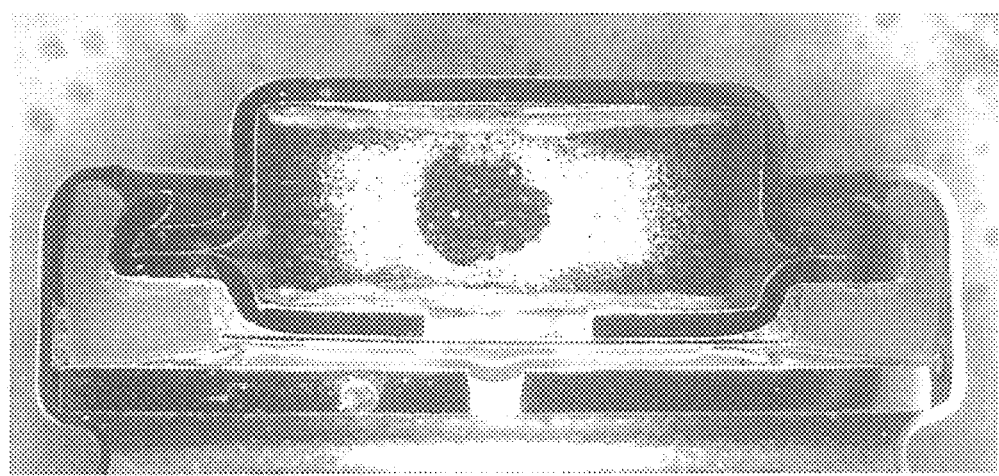
FIG. 11 is a photograph showing a vertical cross section of a relevant part of an electrochemical gas sensor according to a comparative example.

Besides the gas sensor 2 of the present embodiment, a gas sensor was produced by clamping such that the tip end of the side portion 10 was horizontal and parallel to the surface of the bottom plate 4, and the produced gas sensor is referred to as a comparative example. FIG. 10 shows a photograph showing a cross section of the gas sensor of the present embodiment and FIG. 11 shows a photograph showing a cross section of the gas sensor of the comparative example. Referring to the gas sensor of the comparative example, there is a gap between the tip end of the side portion and the gasket so that the range in which the tip end of the side portion and the gasket are hermetically sealed is very small. Also, the bottom surface of the gasket has come away from the bottom plate, and the inner periphery side is tilted upward and the outer periphery side is tilted downward. There is also a gap between the top surface of the bottom portion of the gasket and the outer periphery of the bottom surface of the cover 18. These factors cause variation in hermetic seal property between the inside and the outside of the gas sensor 2 and suggest, for example, the water in the water reservoir may evaporate without passing through the hole 5 of the bottom plate. These factors also suggest that the atmosphere may bypass the cover 18 and arrive at the gas sensor body 14, and it is therefore highly likely that there is also variation in the pressure of the cover 18 pressing the diffusion control plate 16.

Referring to the present embodiment shown in FIG. 10, the tip end of the side portion 10 and the tip end of the gasket 12, as well as the tip end of the gasket 12 and the tip end of the cover 18, are hermetically sealed. Obliquely clamping the tip end of the side portion 10 causes the tip end of the protrusion 26 of the gasket and the tip end of the cover to be obliquely bent, as a result of which these are hermetically clamped to each other. Although the bottom surface of the gasket 12 is slightly tilted from the bottom plate 4, the gap therebetween is small. No gap is observed between the top surface of the gasket 12 and the outer periphery of the bottom surface of the cover 18. Also, it seems that the cover 18 is pressing the diffusion control plate 16 with a uniform downward force by receiving an obliquely downward force, or in other words, a downward force as a whole, from the surrounding elements. Due to these factors, a hermetic seal can be secured between the inside and the outside of the gas sensor 2, and the variation in the shape, the compressive force and the like is small.

Figure 12:
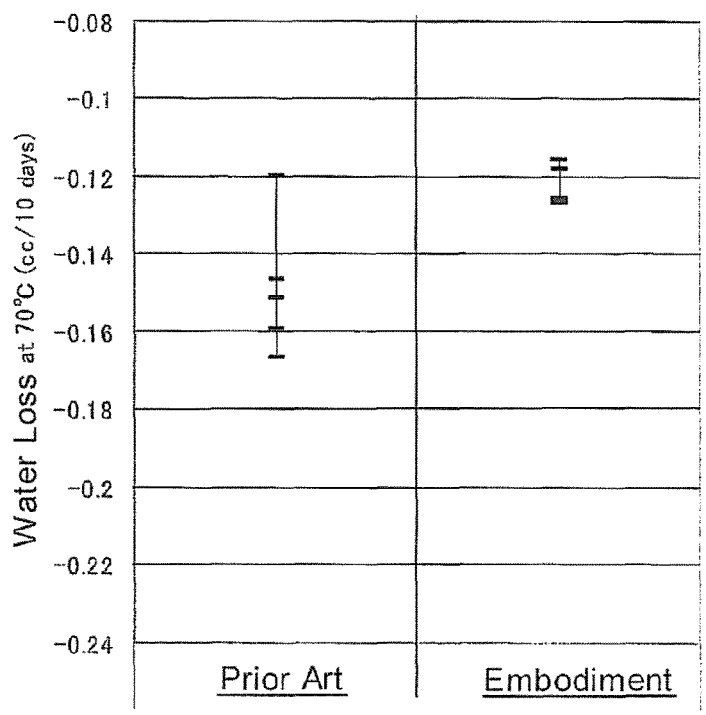
FIG. 12 is a characteristic diagram showing the distribution of water evaporation amount (at 70° C. for 10 days) between the embodiment and the comparative example.

FIG. 12 shows the amount of water evaporated from the water reservoir when the gas sensors of the present embodiment and the comparative example were stored in a dry atmosphere at 70° C. for 10 days. With the comparative example, the evaporation amount varied over a wide range from 0.12 g to 0.17 g, whereas with the present embodiment, the evaporation amount was in a small range of 0.12 g±0.007 g. Wide variations in the evaporation amount result in wide variations in the time required for the water in the water reservoir to be depleted. The water reservoir is provided to supply water vapor to the gas sensor body 14 so as to cause the electrolyte to maintain its conductivity. The variation in the service life of the water reservoir results in variation in the service life of the gas sensor.

Figure 13:
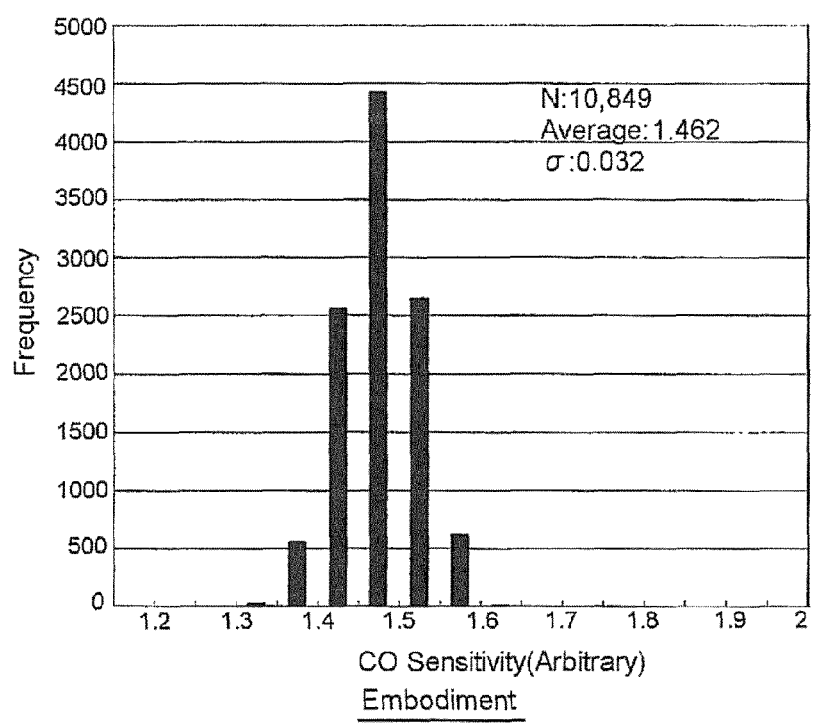
FIG. 13 is a characteristic diagram showing the distribution of CO sensitivity obtained in the embodiment.
Figure 14:
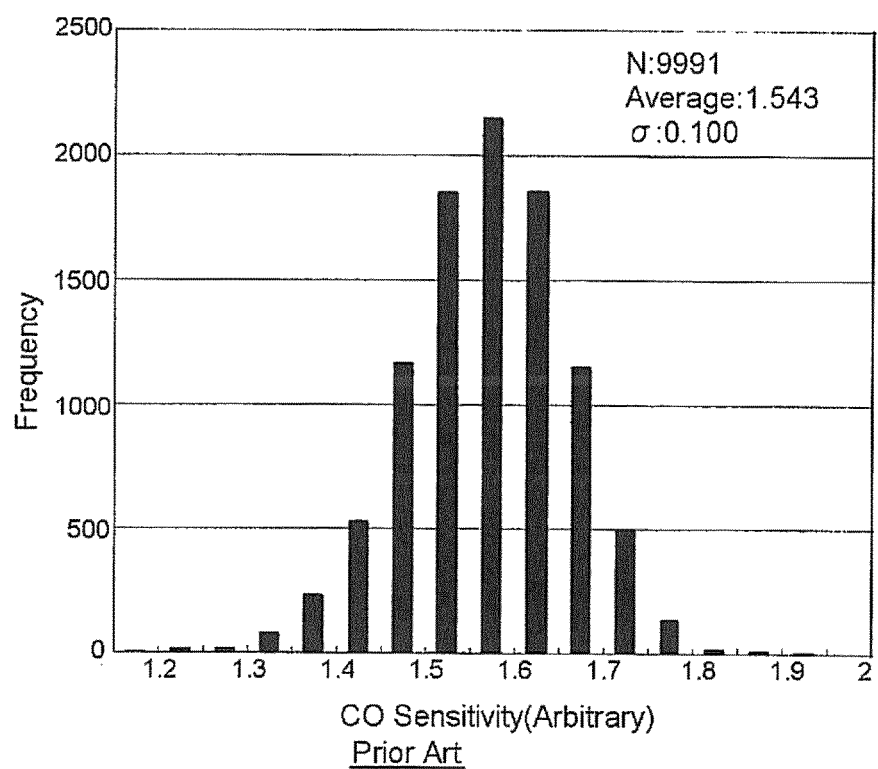
FIG. 14 is a characteristic diagram showing the distribution of CO sensitivity obtained in the comparative example.

FIGS. 13 and 14 respectively show the distributions of CO sensitivity of the gas sensors of the present embodiment (FIG. 13) and the comparative example (FIG. 14). The horizontal axis represents the output current per CO concentration, and the unit is arbitrary. In the present embodiment, the standard deviation of the CO sensitivity distribution is approximately 1/3 of that of the comparative example. Accordingly, the gas sensor of the present embodiment provides uniform gas sensitivity. The electrochemical gas sensor is capable of detecting various types of gases including hydrogen, ethanol and hydrogen sulfide, other than CO.

The present embodiment provides the following effects.

(1) The variation in the water evaporation amount from the water reservoir can be reduced, and as a result the variation in the service life of the gas sensor can be reduced (FIG. 12).

(2) The variation in gas sensitivity can be reduced (FIGS. 13 and 14).

The tip end of the side portion 10 and the protrusion 26 of the gasket 12 are deformed into hermetic contact with the tip end of the protrusion 40 during clamping. The protrusion 40 may be bent during clamping, or it may be initially bent so that the degree of bending during clamping is very small.

DESCRIPTION OF THE NUMERALS

2 Electrochemical Gas Sensor
3 Container
4 Bottom Plate
5 Hole
6 Waist
7 Water Reservoir
8 Water
10 Side Portion
12 Gasket
14 Gas Sensor Body
16 Diffusion Control Plate
17 Diffusion Control Hole
18 Cover
20 to 23 Contact Portion
24 Opening
25 Bottom Portion
26 Protrusion
28 Separator
29 Sensing Electrode
30 Counter Electrode
32, 34 Metal Member
36, 37 Hole
38 Filter member
39 Retaining Sheet
40 Protrusion
42 Mold
43 Hole
44 Surface
46 Container
47 Bottom Portion
48 Protrusion
50 Container
52 Bottom Portion
54 Hole
56 Protrusion
58 Cover
59 Cover
60 Protrusion
D Axial Direction
F Tip End Direction
θ Angle of Inclination

What is claimed is:

1. A method for clamping an electrochemical gas sensor including:
a disc-shaped metal bottom member;
a cylindrical metal side member that extends in at least a first direction along an axial direction of the bottom member so as to surround the bottom member;
a ring-shaped polymer gasket that includes an opening in the center and in which both sides of the opening each have an L-shaped member in cross section;
a gas sensor body including at least a pair of electrodes and a solid electrolyte membrane or a separator retaining a liquid electrolyte; and
a metal cover having a circular bottom surface, the cover including a ring-shaped protrusion provided around periphery of the cover and extending to a side opposite the bottom surface along the axial direction of the cover, the method comprising the steps of:
disposing the gasket, the gas sensor body and the cover on the bottom member such that the one section of the L-shaped member of the gasket is surrounded by the side member and the other section is in contact with the bottom member, that the gas sensor body is located in the opening of the gasket and a bottom surface of the gas sensor body is in contact with the bottom member, and that the bottom surface of the cover covers a top surface of the gas sensor body and the ring-shaped protrusion of the cover extends to a side opposite the bottom member; and
bringing a surface of a hole of a mold tapered to have a larger diameter at front and a smaller diameter at rear into contact with a tip end of the side member, whereby the tip end of the side member and a tip end of the one section of the L-shaped member of the gasket are bent at an acute angle toward the bottom member from the first direction, the tip end of the side member, the tip end of the one section of the L-shaped member of the gasket and a tip end of the protrusion of the cover are in hermetic contact with each other, and the three tip ends are clamped such that none of them is parallel to a surface of the bottom member.

2. An electrochemical gas sensor comprising:
a disc-shaped metal bottom member;
a cylindrical metal side member that extends in at least a first direction along an axial direction of the bottom member so as to surround the bottom member;
a ring-shaped polymer gasket that includes an opening in the center and in which at both sides of the opening each are an L-shaped member in cross section, with one section of the L-shaped member being in contact with an inner side of the side member and the other section of the L-shaped member being in contact with the bottom member;
a gas sensor body that is located in the opening of the gasket and whose bottom surface is in contact with the bottom member, the gas sensor body including at least a pair of electrodes and a solid electrolyte membrane or a separator retaining a liquid electrolyte; and
a metal cover whose bottom surface is circular and is in contact with a top surface of the gas sensor body,
wherein the cover includes a ring-shaped protrusion provided around periphery of the cover and extending to a side opposite the bottom surface along the axial direction of the cover, and
a tip end of the side member and a tip end of the one section of the L-shaped member of the gasket are bent at an acute angle toward the bottom member from the first direction, the tip end of the side member, the tip end of the one section of the L-shaped member of the gasket and a tip end of the protrusion of the cover are in hermetic contact with each other, and none of the tip end of the side member, the tip end of the one section of the L-shaped member of the gasket, and the tip end of the protrusion of the cover is parallel to a surface of the bottom member.

3. The electrochemical gas sensor according to claim 2, wherein the tip end of the side member is angled at 10° to 60° from the first direction.

4. The electrochemical gas sensor according to claim 2, wherein the side member extends in a direction opposite to the first direction from a position of the bottom member and constitutes a bottomed cylindrical container, the bottom member is held by a waist portion of the cylindrical container, water is stored in a bottom space of the cylindrical container that is below the bottom member, and the bottom member is provided with a hole.

* * * * *